United States Patent [19]

Broicher et al.

[11] Patent Number: 4,745,276

[45] Date of Patent: May 17, 1988

[54] DEVICE FOR THE DETECTION OF FLUORESCENT SUBSTANCES ON THE SURFACE OF THE EARTH

[75] Inventors: Heribert Broicher; Erich Kirsch; Friedhart Knolle, all of Goslar; Helmut Winnacker, Ehlershausen; Arthur Zydek, Wolfenbüttel, all of Fed. Rep. of Germany

[73] Assignee: Preussag Aktiengesellschaft Metall, Fed. Rep. of Germany

[21] Appl. No.: 833,099

[22] Filed: Feb. 25, 1986

[51] Int. Cl.[4] .................................. G01N 21/64
[52] U.S. Cl. ......................... 250/253; 250/458.1; 250/461.1
[58] Field of Search .............. 250/253, 461.1, 459.1, 250/458.1; 356/318, 376, 371

[56] References Cited

U.S. PATENT DOCUMENTS

| 3,043,908 | 7/1962 | Madsen | 250/253 |
| 3,527,533 | 9/1970 | Hook et al. | 250/253 |
| 3,736,428 | 5/1973 | Monroe | 356/51 |
| 3,768,908 | 10/1973 | Zaromb | 356/301 |
| 3,899,213 | 8/1975 | Fantasia et al. | 250/461.1 |
| 4,182,574 | 1/1980 | Quillfeldt | 356/318 |
| 4,200,801 | 4/1980 | Schuresko | 250/458.1 |
| 4,236,071 | 11/1980 | Chimenti | 250/253 |
| 7,247,770 | 1/1981 | Welch | 356/318 |
| 4,259,574 | 3/1981 | Carr et al. | 250/461.1 |
| 4,555,627 | 11/1985 | McRae, Jr. | 250/330 |

FOREIGN PATENT DOCUMENTS

| 2947459 | 5/1981 | Fed. Rep. of Germany . |
| 3149728 | 7/1982 | Fed. Rep. of Germany . |
| 17106 | 1/1984 | Japan | 356/371 |
| 27247 | 2/1984 | Japan | 356/371 |
| 794398 | 1/1981 | U.S.S.R. | 356/317 |

OTHER PUBLICATIONS

Cantor, "Electro-Optical Sensor for Measuring Road Surface Texture", SPIE, 178, Smart Sensors, 1979, pp. 127–135.

Scintrex, "Geophysical and Geochemical Instrumentation and Services", (Oct., 1982), Concord, Ontario, Canada.

*Primary Examiner*—Carolyn E. Fields
*Attorney, Agent, or Firm*—Allegretti, Newitt, Witcoff & McAndrews, Ltd.

[57] ABSTRACT

A device for detecting fluorescence on the surface of the earth is disclosed. The device includes a laser installed in a vehicle, means for irradiating an essentially linear surface area in front of and transverse to the vehicle, a directing device for directing the spread beam downward to illuminate the earth's surface and means for detecting fluorescence on the illuminated surface. The inventive device permits the rapid and effective exploration of a relatively large area without gaps of the earth's surface for fluorescent substances.

7 Claims, 4 Drawing Sheets

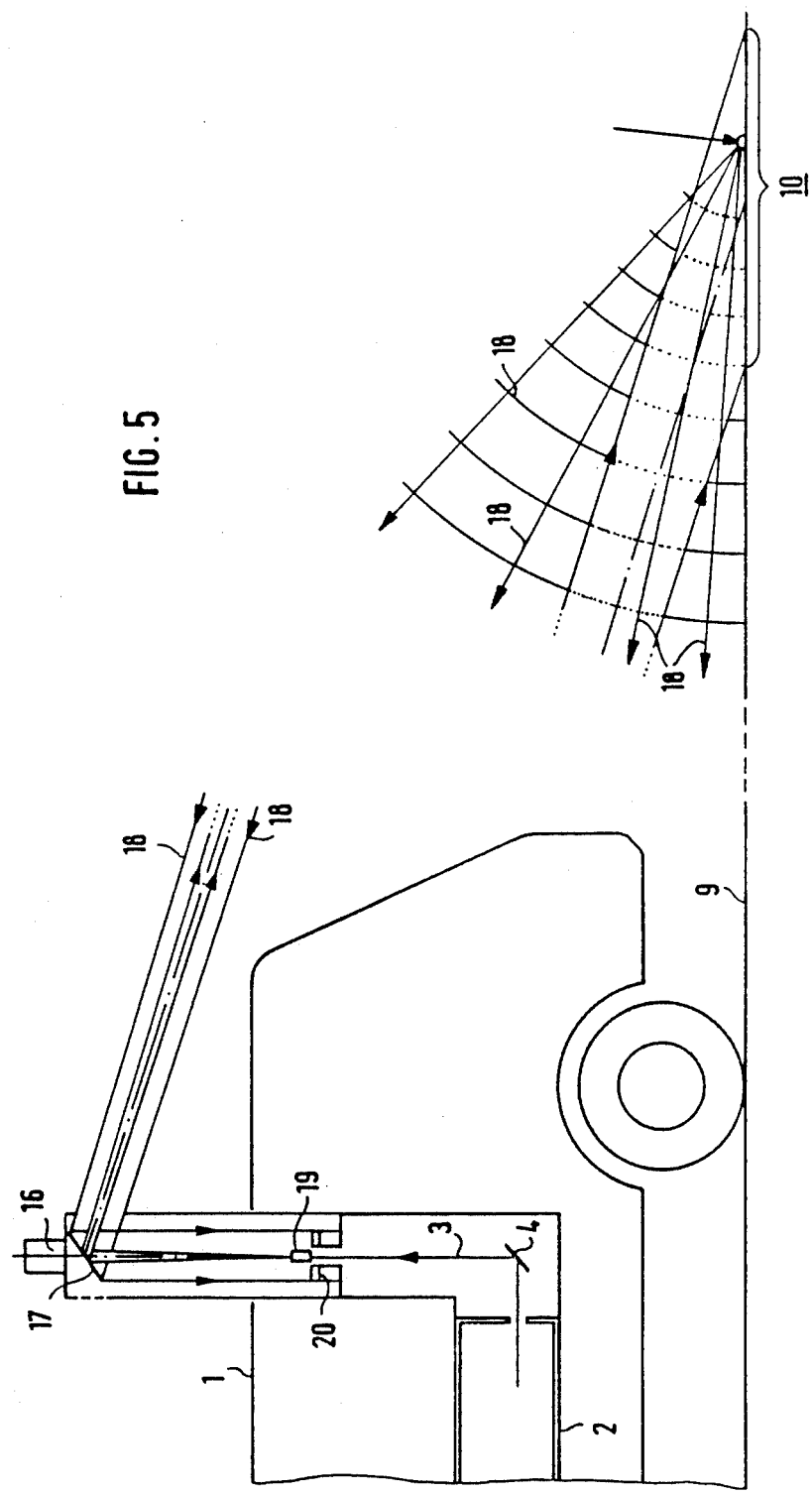

DEVICE FOR THE DETECTION OF FLUORESCENT SUBSTANCES ON THE SURFACE OF THE EARTH

BACKGROUND OF THE INVENTION

1. Field of the Invention

The present invention relates to devices for the detection of fluorescent substances on the surface of the earth.

2. Description of the Prior Art

A device capable of detecting fluorescent substances on the earth's surface is disclosed in a publication by Scintrex, 222 Snidecroft Raod, Concord, Ontario, Canada, dated Oct. 1, 1982. The device is installed in a helicopter and comprises a laser that emits a narrow beam illuminating a limited spot on the surface of the earth. The means for detecting fluorescence comprise an optical system aimed at the illuminated spot. This publication also describes a hand held device of the same type. Whenthis prior art device is used with a helicopter, the distance of the helicopter from the surface of the earth, the helicopter's flying speed, the frequency of the laser (i.e., number of pulses emitted per second), and the size of the illuminated surface area permit the investigation of only very small points. Furthermore, coordination of the surface area sampled from the helicopter with a map is extremely difficult, and requires time-consuming subsequent investigation on the ground. Similarly, the hand held instrument can only illuminate a few square centimeters at a time. Thus, neither of these Scintrex devices is suitable for the exploration of large surface areas on the ground.

SUMMARY OF THE INVENTION

It is an object of the present invention to provide a device that is capable of rapidly, continuously, and systematically exploring the surface of the earth by exciting and detecting fluorescence.

It is a specific object of the present invention to provide a device capable of detecting fluorescent substances throughout a continuous band of the earth's surface as the vehicle carrying the device moves. Preferably, the device is capable of detecting fluorescence in a straight or ring-shaped line, as contrasted with the small points detectable by prior art devices. The position and route followed by the continuous surface band is determined by the route followed by the vehicle. Thus, it is not necessary to aim the device at limited points on the surface of the earth.

Widening or spreading of the laser beam into a broader band to obtain linear illumination is advantageously achieved by means of cylindrical optical systems, in particular by means of a cylindrical lens. It is also possible, however, to use currently available lasers with up to 500 Hz, i.e., up to 500 pulses per second, for obtaining a continuous ring-shaped or ellipse-shaped line by illuminating and investigating overlapping areas. The advantage of such a system, advantageously realized by use of a rotating deflection mirror, is the high energy density of the resulting ultraviolet radiation that excites the flurescence.

The use of a high output of the laser is desirable. However, such lasers are quite heavy. In order to be able to suitably distribute this weight in the vehicle, the laser may be arranged within the vehicle to radiate upwards into a deflection mirror that deflects the laser beam obliquely downward in the general direction in which the vehicle is travelling. Accordingly, the laser beam travels upward from the laser to a point above the vehicle and from there downward in the general direction of investigation. This also makes it possible, where a land vehicle is used, to simply mount the heavy laser on the cargo area of the vehicle.

If a deflecting mirror is used, it is expedient to arrange the means for spreading the beam downstream from the deflecting mirror in the radiation direction. This permits the deflecting mirror to be relatively small, since it only has to deflect a narrow beam rather than a beam spread over a wide sector. In this arrangement, the means for detecting fluorescence may be installed in the vicinity of the deflecting mirror or at the center of the beam sector. In the latter case, it is advantageous to install the means for widening the laser beam and the means for detecting fluorescence at the upper end of an extendable telescopic rod, preferably within a housing. Accordingly, the housing containing the optical system can be extended upward from the vehicle when in use, and may be protected from damage in this position. Its altitude can be adjusted for purposes of correction.

In a further preferred embodiment, partial sectors in the outer edge region of the widened laser beam may be deflected inward by mirrors arranged at the sides of the widened beam band. In this embodiment, the outer edge bands are, in a manner of speaking, pivoted inward. This superposition results in increased radiation intensity in the outer edge regions of the emerging beam sector within which the surface is illuminated. This also makes it possible to equalize the radiation intensity over the emitted beam sector, in contrast to the original widened beam sector in which the radiation intensity decreases from the center towards the edges in approximately a Gaussian distribution curve.

In order to obtain uniform exploration density, the timing frequency of the laser may be directly proportional to the travelling speed of the vehicle. It is preferable for the means for detecting fluorescence to operate with the same timing frequency as the laser.

Further objects and embodiments of the present invention will be described in the following description of the preferred embodiment and the claims.

BRIEF DESCRIPTION OF THE DRAWINGS

FIG. 5 shows another embodiment similar to that shown in FIG. 1 including a land vehicle with a rotating deflecting mirror shown schematically in side elevation.

DESCRIPTION OF THE PREFERRED EMBODIMENT

Figure 1:
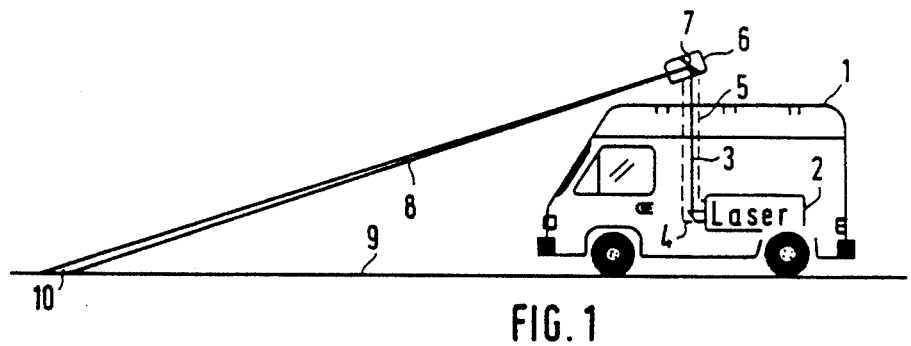
FIG. 1 shows a land vehicle in side elevation provided with a device according to the present invention in schematic representation.
Figure 2:
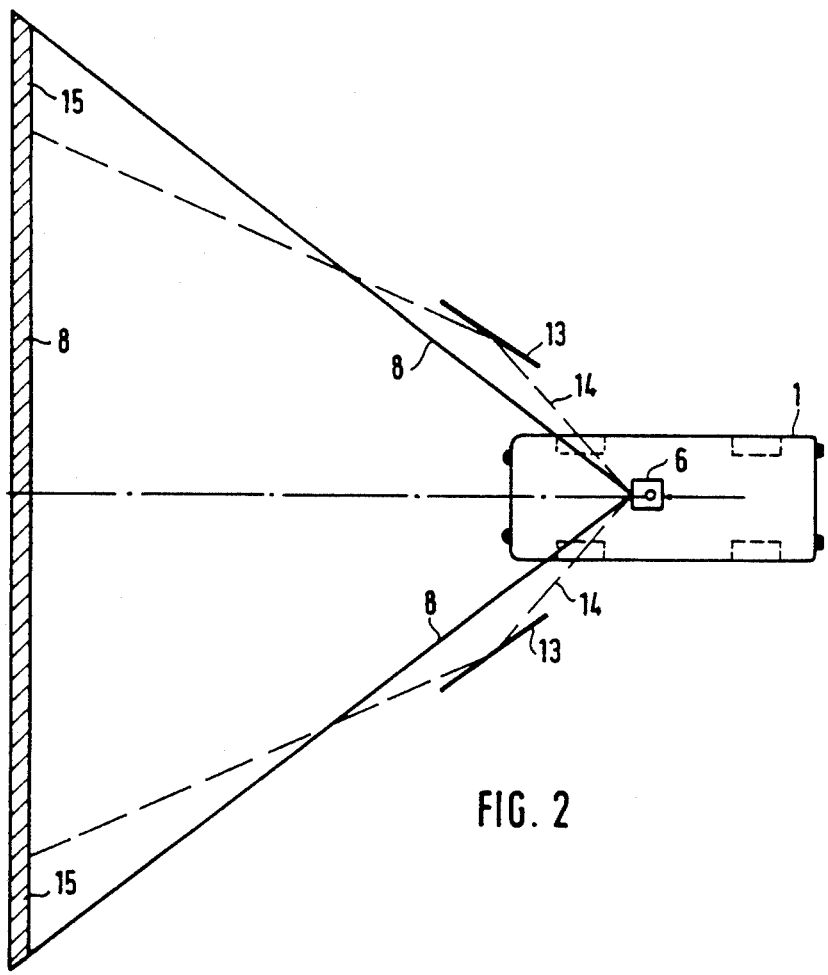
FIG. 2 is a plan view of FIG. 1.

The vehicle shown in FIGS. 1 and 2 is a land vehicle, although it is also possible to use an airplane, a helicopter, or the like. A laser 2 is installed on the loading area of vehicle 1. The laser beam 3 is directed by a mirror 4 upward through an extendable telescopic rod 5 at whose upper end a housing 6 is provided. The housing 6 comprises a deflecting mirror 7 that directs the laser beam in the travelling direction of the vehicle 1 and downward at a shallow angle.

A lens system, not shown in FIGS. 1 and 2, is installed in the housing 6 in front of the deflecting mirror 7 in the travelling direction of vehicle 1. This lens system spreads the laser beam over a sector 8 such that a narrow strip 10 is illuminated in front of vehicle 1 on the ground surface 9 on which vehicle 1 is travelling.

The housing 6 further contains means for detecting fluorescence in the narrow strip, which are not shown here, and comprise, in a manner well known in the art, an optical system, photomultiplier, and evaluating means. A cylindrical lens or other converging lenses may be provided to concentrate the light emitted from the linear strip 10 onto the photomultiplier. In addition, a slit diaphragm is provided that prevents light from entering from regions outside of the narrow strip 10.

Figure 3:
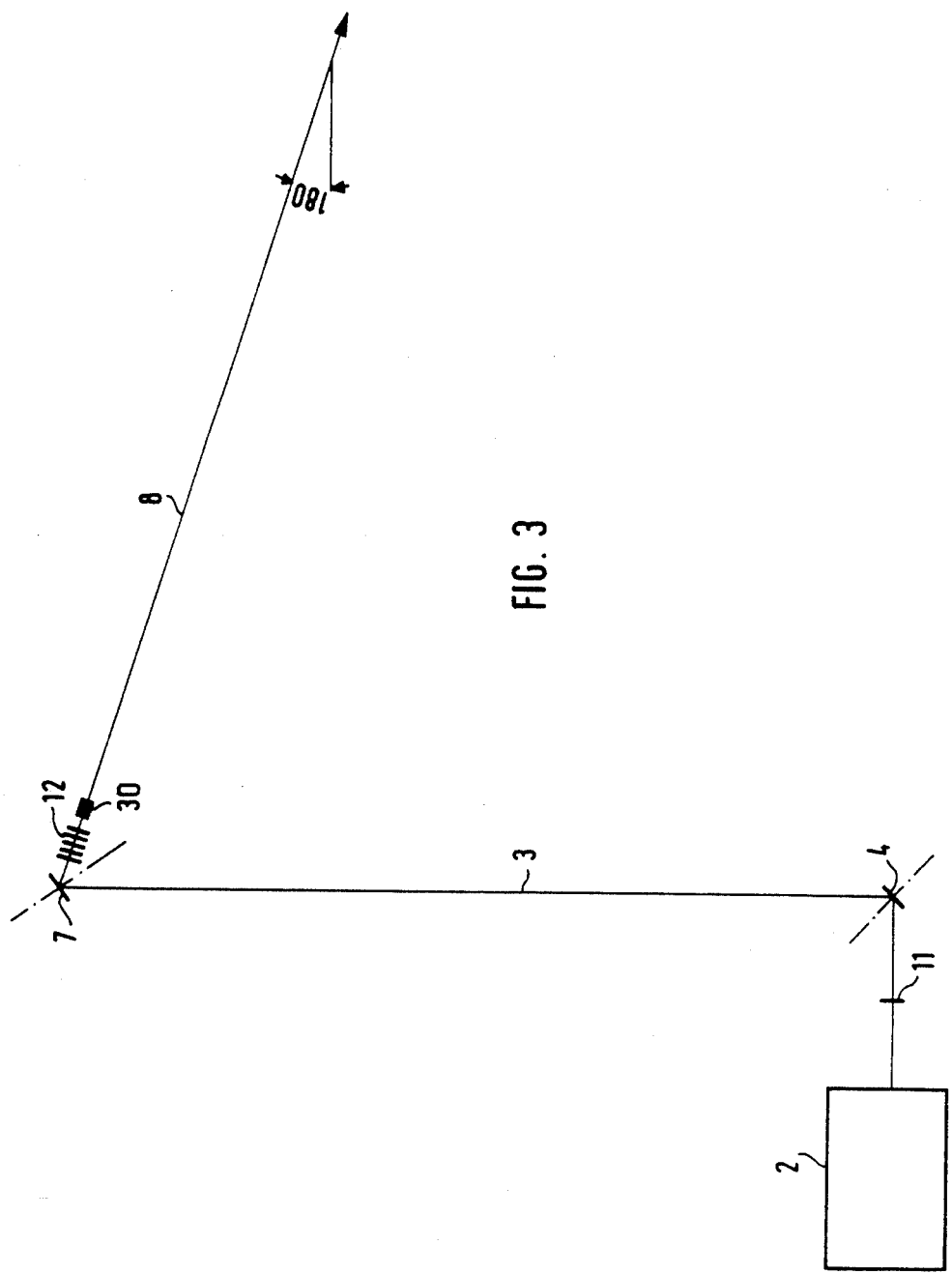
FIG. 3 shows the path followed by the laser beam in the device shown in FIG. 1.

FIG. 3 shows the path followed by the beam and the optical system. The beam 3 emitted from the laser 2 first passes through a lens 11, and is deflected upward by mirror 4 towards the deflecting mirror 7. The mirror 7 deflects the beam obliquely downward such that it impinges upon the surface to be explored at an angle of approximately 18°. Lenses 12 are located downstream from the deflecting mirror 7 in the direction of radiation, with at least one of these lenses 12 being a cylindrical lens (30) that spreads out the beam to form the beam band or sector 8.

Figure 4:
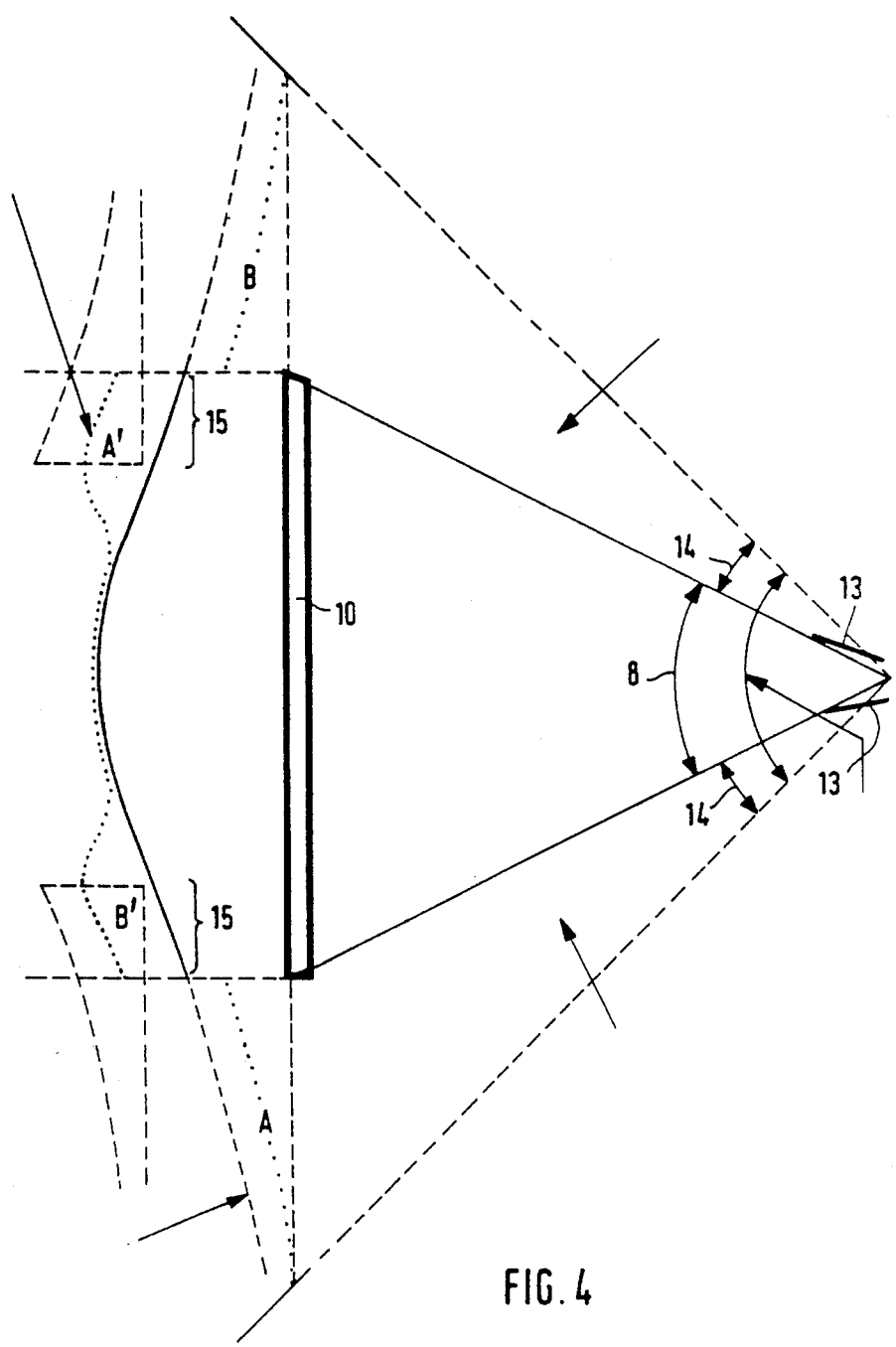
FIG. 4 shows the effect of the reflection of the edge regions of the widened laser beam into the core of the beam sector.

Mirrors 13 are provided adjacent to the beam sector 8 in the same plane, as shown in FIG. 2 and, in particular, in FIG. 4. The dotted lines in FIGS. 2 and 4 indicate that these mirrors 13 deflect the partial sector 14 of the laser beam into the linear strip 10 such that the undeflected and deflected radiation overlaps in regions 15 of strip 10. Accordingly, the intensity of radiation is increased in regions 15 such that the original Gaussian intensity distribution is equalized.

FIG. 5 shows another example of an embodiment similar to that shown in FIG. 1. At the right of FIG. 5, the illuminated strip 10 is shown enlarged. FIG. 5 shows a vehicle 1 in which a device comprising a rotating deflecting mirror 17 driven by motor 16 is installed. The paths followed by the beam 3 emitted by laser 2 and by fluorescent beams 18 are also shown. The beam 3 from laser 2 is spread out by an optical system 19 containing spherical lenses and at least one cylindrical lens. This results in a partial area on the ground surface 9 around the vehicle 1 being illuminated. Fluorescent beams 18 emitted by excited fluorescent substances in the surface 9 being illuminated then pass via the rotating deflecting mirror 17 to an optical receiver 20 arranged surrounding the laser beam 3.

The present invention has been described in terms of certain preferred embodiments. Other embodiments not specifically described may nevertheless fall within the spirit and scope of the present invention and the following claims.

We hereby claim:

1. A device for detecting fluorescent substances on a surface area of the earth, comprising a vehicle, a pulsating laser for illuminating the surface area by generating a beam, the laser being installed in the vehicle, means for irradiating an essentially linear surface on a strip in front of and transverse to the vehicle, the means for irradiating having a cylindrical lens for diffusing the beam of the laser into a fan-shaped beam in a plane at a shallow angle to the horizontal to illuminate a linear strip transverse to the direction of movement of the vehicle and a directing device for directing the fan-shaped beam of the laser in front of the vehicle at the surface area of the earth, and means for detecting fluorescence emitted by the entire linear surface area strip illuminated by the beam, said means for detecting being positioned in the vicinity of the directing device so as to be sensitive to fluorescence emitted at said shallow angle to the horizontal.

2. The device according to claim 1 wherein the directing device comprises a deflecting mirror that is capable of deflecting the beam obliquely downward in the traveling direction of the vehicle, the cylindrical lens being arranged downstream from the deflecting mirror.

3. The device according to claim 2 wherein the deflecting mirror, the cylindrical lens, and the means for detecting fluorescence are installed in a common housing mounted on the top of an extendable telescopic tube.

4. The device according to claim 1 wherein the laser is installed in a cargo area of the vehicle.

5. The device according to claim 1 wherein at least one mirror is provided downstream from the cylindrical lens, the at least one mirror being capable of deflecting a lateral edge portion of the fan-shaped laser beam into a portion of the undeflected beam such that a laser beam of essentially uniform intensity over the illuminated surface area is obtained.

6. The device according to claim 1 wherein the pulsing frequency of the laser is directly proportional to the traveling speed of the vehicle.

7. The device according to claim 1 wherein the means for detecting fluorescence includes a slit diaphragm that prevents light from regions outside of the illuminated surface area from being detected.

* * * * *